United States Patent [19]
Leschinsky et al.

[11] Patent Number: 6,146,372
[45] Date of Patent: Nov. 14, 2000

[54] APPARATUS AND METHOD FOR THE PERCUTANEOUS INSERTION OF A PEDIATRIC INTRA-AORTIC BALLOON CATHETER

[75] Inventors: Boris Leschinsky, Waldwick, N.J.; Sidney Wolvek, Brooklyn, N.Y.

[73] Assignee: Datascope Investment Corp, Montvale, N.J.

[21] Appl. No.: 09/220,400

[22] Filed: Dec. 24, 1998

[51] Int. Cl.⁷ .................................................. A61M 31/00
[52] U.S. Cl. ........................... 604/510; 604/96; 604/264
[58] Field of Search ............................. 604/96, 102, 104, 604/192, 198, 264, 507, 508, 509, 510, 523, 528; 606/191–198

[56] References Cited

U.S. PATENT DOCUMENTS

| | | | |
|---|---|---|---|
| 4,327,709 | 5/1982 | Hanson et al. .............................. | 128/1 |
| 4,682,981 | 7/1987 | Suzuki et al. ............................. | 604/158 |
| 4,850,969 | 7/1989 | Jackson ..................................... | 604/96 |
| 5,324,257 | 6/1994 | Osborne et al. ........................... | 604/53 |
| 5,383,853 | 1/1995 | Jung et al. ................................. | 604/96 |
| 5,395,332 | 3/1995 | Ressemann et al. ....................... | 604/96 |
| 5,443,457 | 8/1995 | Ginn et al. ................................. | 604/280 |
| 5,752,932 | 5/1998 | Ellis et al. .................................. | 604/96 |
| 5,984,945 | 11/1999 | Sirhan ....................................... | 606/194 |

*Primary Examiner*—Glenn K. Dawson
*Assistant Examiner*—Catherine Serke
*Attorney, Agent, or Firm*—Abraham P. Ronai

[57] ABSTRACT

A method for percutaneously inserting an improved pediatric intra-aortic balloon. The improvement comprises a soft tip having a self occluding lumen capable of accommodating a guide wire. A removable pull tube is disposed within the self occluding lumen to prevent occlusion of the self occluding lumen. The catheter is designed without a guide wire lumen so as to be capable of rapid inflation and deflation of the balloon. The method comprises the following steps:

(a) inserting an angiographic needle into the aorta;
(b) passing the guide wire through the needle into the aorta;
(c) removing the needle;
(d) disposing the pull tube about the proximal end of the guide wire;
(e) removing the pull tube from the self occluding lumen;
(f) advancing the catheter into the aorta;
(g) removing the guide wire from the aorta;
(h) advancing the catheter up the aortic passageway to a position appropriate for pumping.

18 Claims, 6 Drawing Sheets

APPARATUS AND METHOD FOR THE PERCUTANEOUS INSERTION OF A PEDIATRIC INTRA-AORTIC BALLOON CATHETER

BACKGROUND OF THE INVENTION

1. Field of the Invention

The invention relates to a single lumen intra-aortic balloon catheter. More particularly, the invention relates to a single lumen intra-aortic balloon catheter designed for percutaneous insertion into the aorta of an infant.

2. Description of the Prior Art

Intra-aortic balloon pumping (IABP) is a recognized technique for cardiac assistance for a failing heart. It has become a standard mode of treatment for perioperative low cardiac output syndrome and cardiogenic shock after myocardial infarction in adults. Further, it has been used for such purposes as helping to wean an adult patient away from cardiopulmonary bypass, and to support a patient during a difficult postoperative period. Each year since 1968, the IABP has been used with increasing frequency on an estimated 100,000 adults. The only pediatric IAB catheter currently on the market is produced by Datascope Corp. The success of the Datascope pediatric IAB is reflected in several studies. See, for example, *Intra-aortic balloon pumping in children* by Webster and Veasy in Heart & Lung: The Journal of Critical Care (1985) and *Intra-aortic balloon pumping in infants and children* by Veasy, Blalock, Orth, and Boucek in Therapy and Prevention (1983). The major problem with the present state of the art pediatric catheter, however, is the fact that it must be inserted surgically. Due to design limitations imposed by the dimensions of an infant's femoral artery the pediatric IAB catheter is too small to accommodate a lumen for a guide wire.

A guide wire facilitates percutaneous insertion by guiding the catheter into the insertion site in the artery. When a guide wire is used it is generally inserted through a lumen in an angiographic needle and into the artery. After the needle is removed, the guide wire is already in the artery to guide the balloon into the artery.

The femoral artery has heretofore been used for insertion of the present state of the art balloon catheters because of the large diameter of that artery. However, due to the relatively large entering cross-section of the state of the art pediatric IAB catheter, and the relatively small pediatric femoral artery diameter, guide wire insertion through a guide wire in the catheter cannot be performed. Considerable and rather delicate surgery must be performed in order to reach and isolate the femoral artery in a manner which enables the balloons to be introduced. Surgical insertion of the IAB catheter generally takes as long as thirty minutes. In many cases, only vascular surgeons are willing or able to undertake this surgery, thus limiting the use of the otherwise advantageous pediatric IAB catheter. Furthermore, considerable difficulty is often encountered in the healing of these surgical incisions because of their location in the groin.

Currently, IABs for adults are non-surgically inserted through a sheath positioned in the femoral artery. Many attempts have been to minimize the size of the sheath so as to ease insertion of the sheath and to facilitate healing of the insertion site. Unfortunately, an infant's femoral artery is too small to accommodate a sheath large enough to be used with the pediatric IAB. Therefore, the need exists for a sheathless method for inserting a pediatric IAB.

Considering the complexity and the time consuming nature of a surgical IAB catheter insertion procedure and the fact that surgical incisions made in the groin area are difficult to heal, the need exists for a pediatric IAB catheter capable of being inserted percutaneously.

While the present state of the art pediatric IAB catheter may be suitable for the particular purpose employed, or for general use, it would not be as suitable for the purposes of the present invention as disclosed hereafter.

SUMMARY OF THE INVENTION

Accordingly, it is an object of the invention to produce a pediatric intra-aortic balloon catheter which is capable of being inserted percutaneously and sheathlessly.

It is another object of the invention to produce a method for percutaneously inserting said pediatric intra-aortic balloon catheter.

It is yet another object of the invention to produce a pediatric intra-aortic balloon catheter without a guide wire lumen through the catheter which is capable of being inserted percutaneously.

It is a further object of the invention to take advantage of an infant's shallow artery depth to produce a pediatric IAB catheter that is flexible enough to be advanced through an infant's delicate arterial passageway.

It is still a further object of the invention to produce a pediatric intra-aortic balloon catheter, without a guide wire lumen, capable of rapid inflation and deflation of the balloon to accommodate a generally high infant's heart rate.

The invention is a method for percutaneously inserting an improved pediatric intra-aortic balloon. The improvement comprises a soft tip having a self occluding lumen capable of accommodating a guide wire. A removable pull tube is disposed within the self occluding lumen to prevent occlusion of the self occluding lumen prior to insertion. The catheter is designed without a guide wire lumen so as to be capable of rapid inflation and deflation of the balloon. The method comprises the following steps:

(a) inserting an angiographic needle into the aorta;

(b) passing the guide wire through the needle a short distance into the aorta;

(c) removing the needle;

(d) disposing the pull tube about the proximal end of the guide wire;

(e) removing the pull tube from the self occluding lumen;

(f) advancing the catheter into the aorta;

(g) removing the guide wire from the aorta;

(h) advancing the catheter up the aortic passageway to a position appropriate for pumping.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
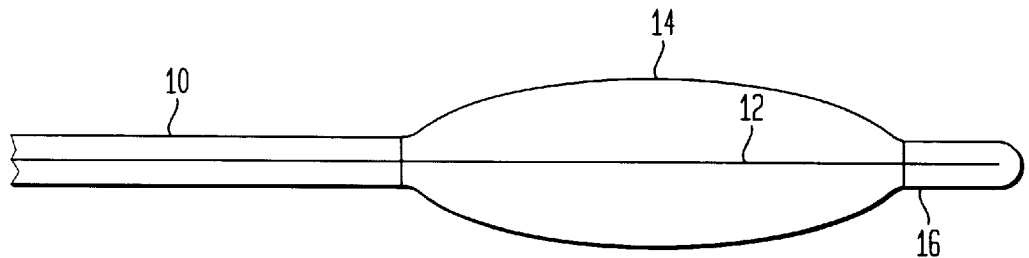
FIG. 1 is longitudinal cross section of a state of the art pediatric IAB catheter.

FIG. 1 illustrates a current state of the art pediatric intra-aortic balloon (IAB) catheter comprising a catheter 10, a balloon membrane 14, a stiffening member 12, and a tip 16, each having distal and proximal ends. The proximal end of the balloon membrane 14 is attached to the distal end of the catheter 10. The distal end of the balloon membrane 14 is attached to the proximal end of the tip 16. The stiffening member 12 is disposed within the catheter 10, the balloon membrane 14, and the tip 16. The distal end of the stiffening member 12 is fixed inside the tip 16. The balloon membrane 14, in its inflated state, has a volume of between 1 and 25 cubic centimeters. Gas (Helium) pumped through the catheter 10 and into the balloon membrane 14 is used to inflate and deflate the balloon membrane 14. The proximal end of the state of the art pediatric intra-aortic balloon catheter is not shown in FIG. 1.

The femoral artery has heretofore been used for insertion of the state of the art balloon catheters because of the relatively large diameter of that artery. However, due to the relatively large entering cross-sections of the prior art pediatric IAB catheters, and the relatively small diameter of the pediatric femoral artery, considerable and rather delicate surgery must be performed in order to reach and isolate the femoral artery in a manner which enables the balloons to be introduced. In many cases, only vascular surgeons are willing or able to undertake this surgery, thus limiting the use of the otherwise advantageous pediatric IAB catheter. Furthermore, considerable difficulty is often encountered in the healing of these surgical incisions because of the increased possibility of infection due to their location in the groin.

Surgical insertion of pediatric IAB catheters has been necessary because they are too small to accommodate a guide wire lumen, which would facilitate a percutaneous insertion. In contrast, IAB catheters for adults are generally made large enough to dispose within the body of the catheter a guide wire lumen. A guide wire facilitates a percutaneous insertion in adults in two ways. First, it guides the catheter into the insertion site in the artery. When a guide wire is used it is generally inserted through a lumen in an angiographic needle and into the artery. After the needle is removed, the guide wire is already in the artery to guide the balloon into the artery. Second, a guide wire facilitates tracking of the catheter in the often tortuous aortic pathway.

Figure 2A:
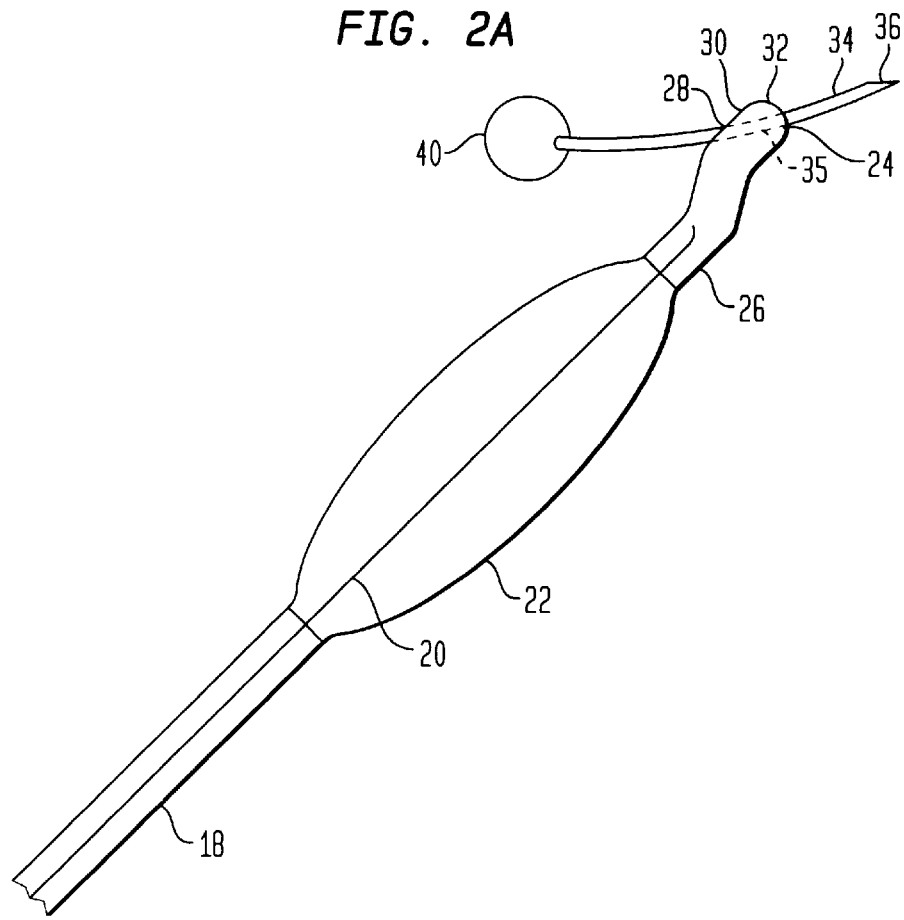
FIG. 2A is longitudinal cross section of an improved pediatric IAB catheter.

FIG. 2A illustrates an improved pediatric intra-aortic balloon catheter which is small enough to be inserted percutaneously and yet still capable of accommodating a guide wire. A guide wire is important for percutaneous insertion of a pediatric IAB catheter primarily for insertion reasons. The aortic pathway of a child does not demonstrate the same tortuosity as the adult aortic path nor does it contain obstructions caused by atherosclerosis disease. Therefore, a guide wire is not necessary to facilitate tracking of the catheter in the aorta. Rather it is only necessary to serve as a guide through the skin and subcutaneous tissue into the femoral artery. The improved pediatric IAB catheter comprises a catheter 18, a balloon membrane 22 (shown in its inflated state), a stiffening member 20, a tip 24, and a pull tube 34 having a proximal end, a distal end, a central portion 35, and a pull tube lumen 36 which extends from the proximal end to the distal end of the pull tube 34. The catheter 18, balloon membrane 22, and the stiffening member 20 each have proximal and distal ends. The tip 24 has a first proximal end 26, a second proximal end 28, and a distal end 30. Similar to the state of the art catheters, the proximal end of the balloon membrane 22 is attached to the distal end of the catheter 18. The distal end of the balloon membrane 22 is attached to the first proximal end 26 of the tip 24. The stiffening member 20 is disposed within the catheter 18, the balloon membrane 22, and the tip 24. The balloon membrane 22 when inflated has a volume of 1 to 25 cubic centimeters. The distal end of the stiffening member 20 is fixed inside the tip 24 and may follow the contours of the tip 24. The tip 24 has a "flattened S" shape and a self occluding lumen 32 which extends at an angle from a first point on the distal end 30 of the tip 24 to a second point on the second proximal end 28 of the tip 24 which is further away from the catheter 18 axis than the first point. The central portion 35 of the pull tube 34 is disposed within the self occluding lumen 32. A ring 40 is attached to the proximal end of the pull tube 34. The tip 24 is made from a flexible material such as silicone or polyurethane. One advantage of using polyurethane for the tip 24 material is that it matches the material of the balloon membrane 22, and therefore, allows for a simpler balloon membrane 22 to tip 24 bond.

The design of the improved pediatric IAB catheter takes advantage of the fact that infants have shallow artery depths. A shallow artery depth allows the physician to hold and apply insertion pressure to the catheter closer to the arterial insertion site. Applying insertion pressure closer to the insertion site reduces the chances of the IAB catheter buckling. Since there is a reduced chance of buckling the pediatric IAB catheter can be made more flexible than the adult IAB catheter.

Furthermore, the fact that an infant's arteries are not obstructed by atherosclerosis and that a pediatric IAB catheter does not have to be stiff enough to withstand buckling when being inserted past an obstruction also allows for the use of a more flexible pediatric IAB catheter without a sheath. It is important for pediatric IAB catheters to be as flexible as possible to prevent harm to or even penetration of the delicate infant vasculature.

Note that the improved pediatric IAB is designed without a guide wire lumen. A guide wire lumen generally impedes rapid inflation and deflation of the balloon membrane 22 by reducing the gas path area. Rapid inflation and deflation of the balloon membrane 22 is necessary to accommodate an infant's high heart rate.

Figure 2B:
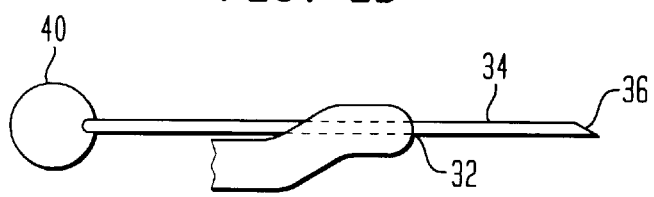
FIG. 2B is longitudinal cross section of an alternate tip embodiment for the improved pediatric IAB catheter of FIG. 2A.

FIG. 2B illustrates an alternate tip embodiment. The alternate tip is shown with the central portion 35 of the pull tube 34 disposed within the self occluding lumen 32. The self occluding lumen 32, rather than extending at an angle from the distal end 30 of the tip 24 to the second proximal end 28 of the tip 24, as shown in FIG. 2A, extends parallel to axis of the catheter 18.

Figure 3A:
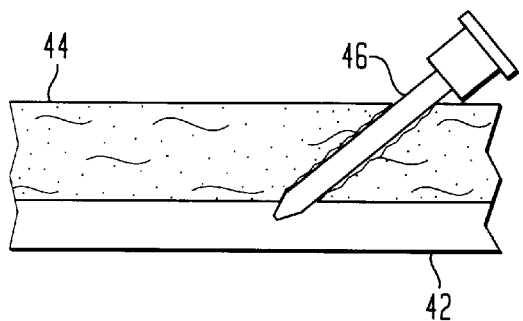
FIG. 3A is a longitudinal cross section of an infant's leg illustrating the first insertion step of the improved IAB catheter: insertion of an angiographic needle.
Figure 3B:
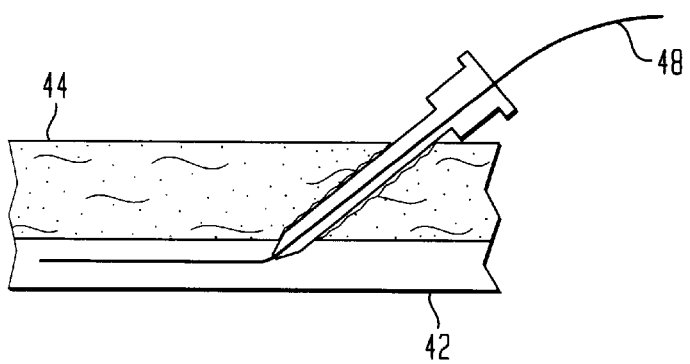
FIG. 3B is a longitudinal cross section of an infant's leg illustrating the second insertion step of the improved IAB catheter: insertion of a guide wire.
Figure 3C:
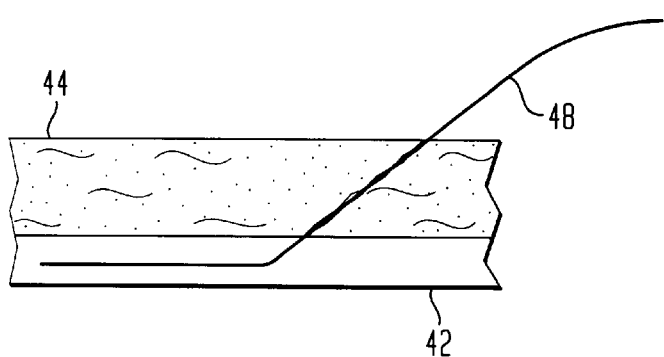
FIG. 3C is a longitudinal cross section of an infant's leg illustrating the third insertion step of the improved IAB catheter: removal of the angiographic needle.
Figure 3D:
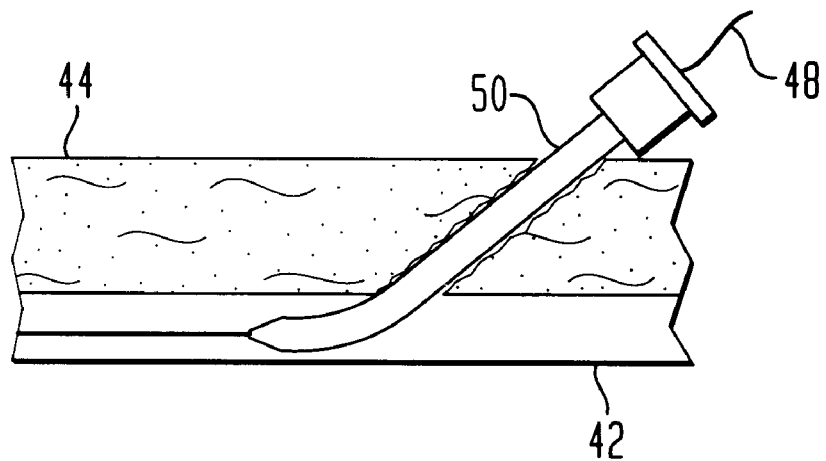
FIG. 3D is a longitudinal cross section of an infant's leg illustrating the fourth insertion step of the improved IAB catheter: insertion of a dilator.
Figure 3E:
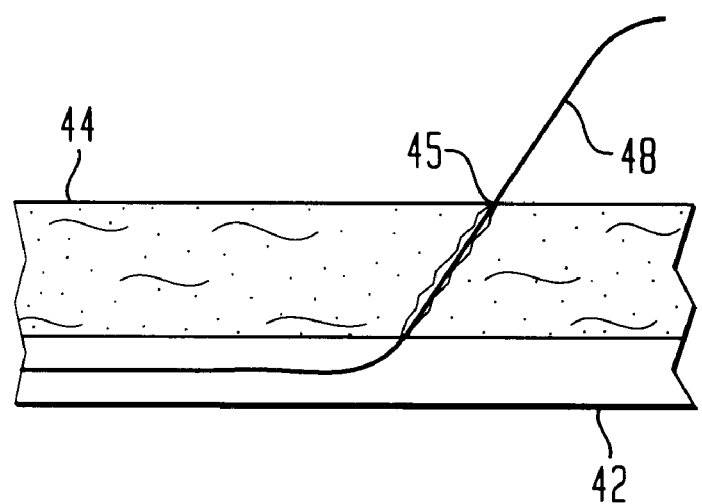
FIG. 3E is a longitudinal cross section of an infant's leg illustrating the fifth insertion step of the improved IAB catheter: removal of the dilator.
Figure 3F:
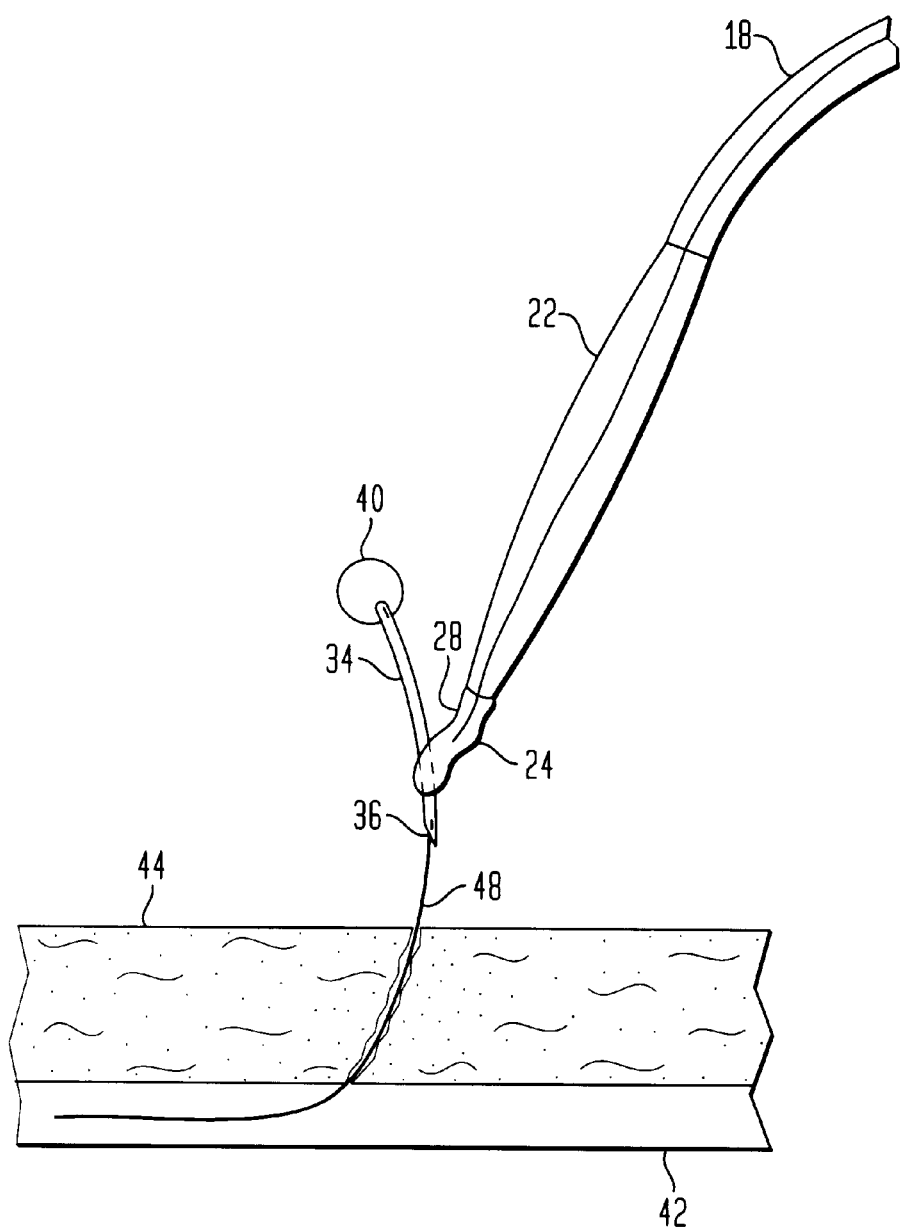
FIG. 3F is a longitudinal cross section of an infant's leg and the improved IAB catheter illustrating the sixth insertion step of the improved IAB catheter: insertion of the guide wire into a pull tube.
Figure 3G:
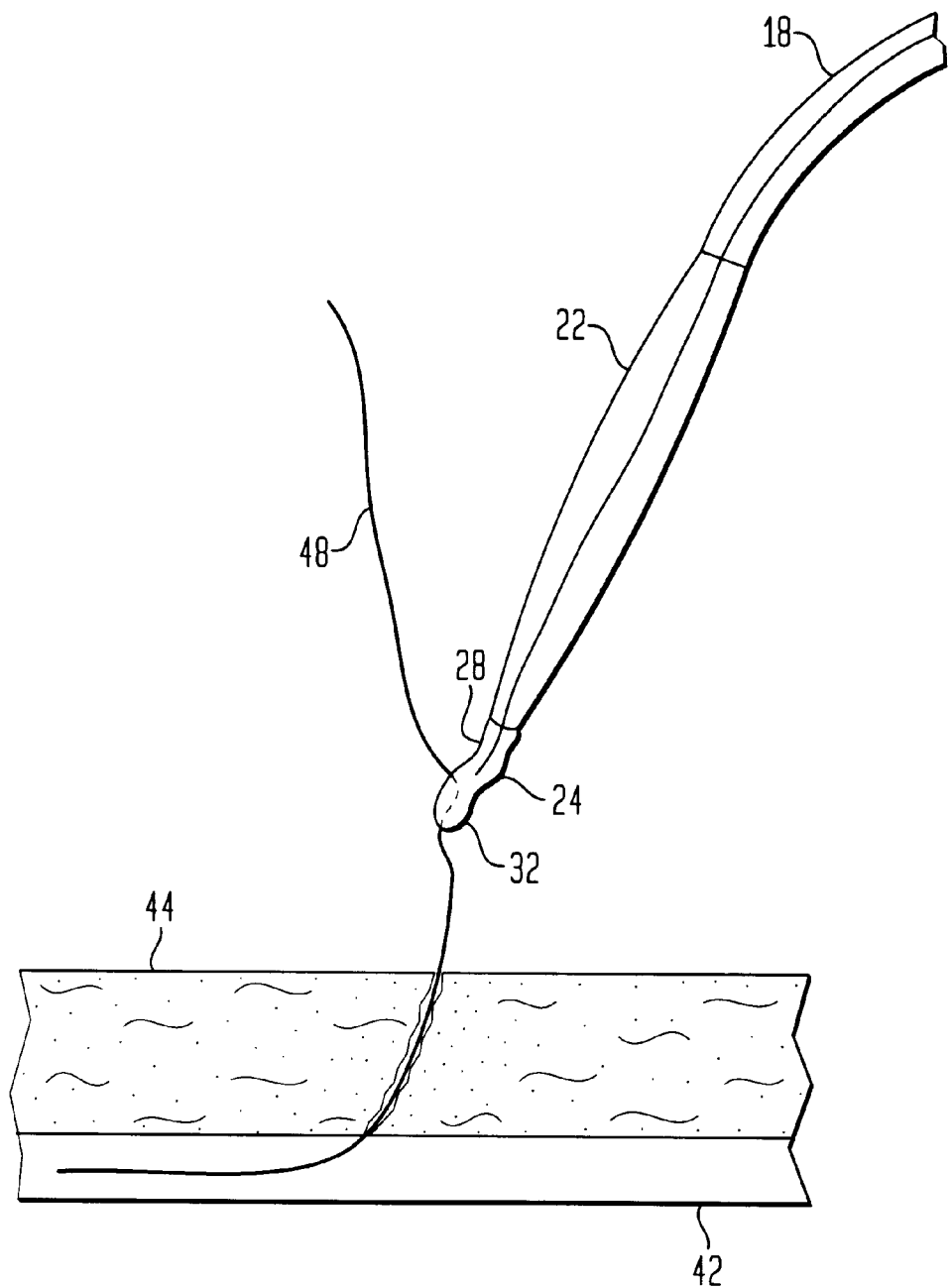
FIG. 3G is a longitudinal cross section of an infant's leg and the improved IAB catheter illustrating the seventh insertion step of the improved IAB catheter: removal of the pull tube.
Figure 3H:
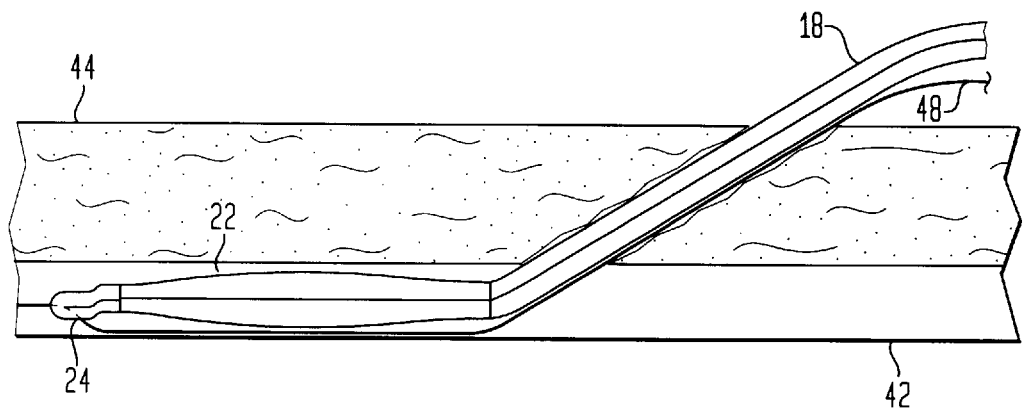
FIG. 3H is a longitudinal cross section of an infant's leg illustrating the eighth insertion step of the improved IAB catheter: advancing the IAB catheter into the artery.
Figure 3I:
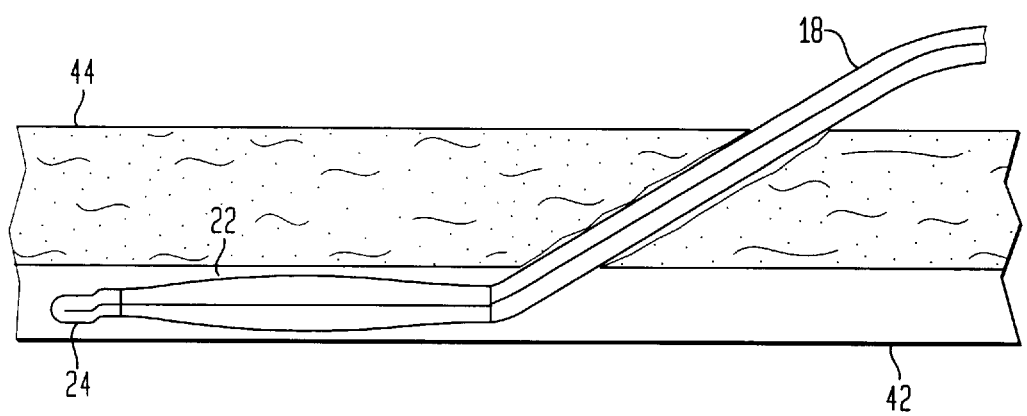
FIG. 3I is a longitudinal cross section of an infant's leg illustrating the ninth insertion step of the improved IAB catheter: removal of the guide wire.

FIGS. 3A–3I are longitudinal cross sections of an infants leg which illustrate a method of inserting the improved pediatric IAB catheter herein disclosed. The cross sections are focused on the area immediately surrounding the insertion site of the catheter. FIG. 3A illustrates the first insertion step, which involves inserting an angiographic needle 46 into a femoral artery 42 of a pediatric patient having a skin line 44. FIG. 3B illustrates the second insertion step, which involves inserting a guide wire 48 through the angiographic needle 46 and into the artery 42. The guide wire 48 is not advanced through the artery all the way to the final position of the catheter. Rather, only a short length of the guide wire 48 is inserted into the artery to facilitate insertion of the catheter. The guide wire 48 is not necessary to guide the catheter through the relatively straight aortic path present in the pediatric patient. FIG. 3C illustrates the state of the procedure after completion of the third insertion step, which involves removing the angiographic needle 46. FIG. 3D illustrates the fourth insertion step, which involves dilating the artery 42 by inserting a flexible dilator 50 into the artery 42. The dilator 50 is disposed about the guide wire 48. FIG. 3E illustrates the state of the procedure after completion of the fifth insertion step, in which the dilator 50 is removed. Note that the insertion channel 45 has widened considerably as a result of the dilating in step four. FIG. 3F illustrates the sixth insertion step, which involves disposing the pull tube 34 about the guide wire 48 by inserting the proximal end of the guide wire 48 into the distal end of the pull tube lumen 36 and pushing the entire catheter forward until the proximal end of the guide wire 48 extends beyond the second proximal end 28 of the tip 24. The distal end of the pull tube 34 may be sealed, in which case, the distal end of the guide wire 48 cannot extend beyond the distal end of the pull tube 34. Further note that the proximal end of the pull tube 34 is cut at an angle to facilitate insertion of the guide wire 48. FIG. 3G illustrates the state of the procedure after the completion of the seventh insertion step, which comprises pulling the pull tube 34 out of the self occluding lumen 32. Removal of the pull tube 34 can be accomplished by pulling the ring 40, as shown in FIG. 3F, along the axis of the pull tube 34, away from the pediatric patient. FIG. 3H illustrates the state of the procedure after the eighth insertion step is completed. The eighth insertion step comprises sliding the IAB catheter into the artery 42 guided by the guide wire 48. FIG. 3I illustrates the state of the procedure after completion of the ninth insertion step, which comprises removing the guide wire 48 from the artery 42. The IAB is then advanced along the artery 42 of the patient so as to position the catheter for pumping.

The tip 24 is made form either silicone or polyurethane both of which display a special property: If a needle is pulled through a piece of either of these materials any hole or lumen formed will self occlude. Therefore, in insertion step nine (shown in FIG. 3I), as soon as the guide wire 48 is removed the self occluding lumen 32 occludes. The self occluding lumen is an important feature of the tip 24 because it prevents blood from accumulating and possibly forming embolus in the self occluding lumen 32.

What is claimed is:

1. A single lumen intra-aortic balloon catheter comprising a catheter having distal and proximal ends, a balloon membrane having distal and proximal ends, and a tip, the proximal end of the balloon membrane being connected to the distal end of the catheter, the tip has a first proximal end, a second proximal end, a distal end, and a second lumen for accommodating a guide wire which extends from said distal end of the tips to said second proximal end and which self occludes along its entire length after the guide wire is removed, the distal end of the balloon membrance is connected to the first proximal end of the tip.

2. The single lumen intra-aortic balloon catheter as claimed in claim 1 wherein the tip is made from an elastic biocompatible polymer.

3. The single lumen intra-aortic balloon catheter as claimed in claim 2 wherein the tip is made from polyurethane.

4. The single lumen intra-aortic balloon catheter as claimed in claim 2 wherein the catheter has a longitudinal axis and wherein the second lumen extends at an angle from a first point on the second proximal end of the tip to a second point on the distal end of the tip which is closer to the longitudinal axis of the catheter than the first point.

5. The single lumen intra-aortic balloon catheter as claimed in claim 2 wherein the catheter has a longitudinal axis and wherein the second lumen extends parallel to the longitudinal axis of the catheter.

6. The single lumen intra-aortic balloon catheter as claimed in claim 1 further comprising a pull tube removably disposed within the second lumen and having a pull tube lumen which extends the entire length of the pull tube and which is capable of accommodating a guide wire, said pull tube being removed from within the second lumen prior to insertion of the intra-aortic balloon catheter into a patient.

7. The single lumen intra-aortic balloon catheter as claimed in claim 6 wherein the pull tube comprises a tube, and a gripper which is disposed about and attached to the tube.

8. The single lumen intra-aortic balloon catheter as claimed in claim 6 wherein the second lumen is self occluding.

9. The single lumen intra-aortic balloon catheter as claimed in claim 6 wherein the tip is made from an elastic biocompatible polymer.

10. The single lumen intra-aortic balloon catheter as claimed in claim 6 wherein the tip is made from polyurethane.

11. The single lumen intra-aortic balloon catheter as claimed in claim 7 wherein the catheter has a longitudinal axis and wherein the second lumen extends at an angle from a first point on the second proximal end of the tip to a second point on the distal end of the tip which is closer to the longitudinal axis of the catheter than the first point.

12. The single lumen intra-aortic balloon catheter as claimed in claim 6 wherein the catheter has a longitudinal axis and wherein the second lumen extends parallel to the longitudinal axis of the catheter.

13. A method for inserting a single lumen intra-aortic balloon catheter comprising a catheter having distal and proximal ends, a balloon membrane having distal and proximal ends, and a tip, the proximal end of the balloon membrane is connected to the distal end of the catheter, the tip has a first proximal end, a second proximal end, a distal end, and a second lumen for accommodating a guide wire which extends from said distal end of the tip to said second proximal end and which self occludes along its entire length after the guide wire is removed the distal end of the balloon membrance is connected to the first proximal end of the tip, comprising the steps of:

(a) passing a distal end of a guide wire into an artery;

(b) passing a proximal end of the guide wire through the second lumen;

(c) advancing the catheter into the artery;

(d) removing the guide wire from the artery;

(e) advancing the catheter without the assistance of the guide wire up the aortic passageway to a position appropriate for pumping.

14. A method for inserting a single lumen intra-aortic balloon catheter comprising a catheter having distal and proximal ends, a balloon membrane having distal and proximal ends, a tip, and a pull tube, the proximal end of the balloon membrane is connected to the distal end of the catheter, the tip has a first proximal end, a second proximal end, a distal end, and a second lumen for accommodating a guide wire which extends from said distal end of the tip to said second proximal end, the distal end of the balloon membrance is connected to the first proximal end of the tip, the pull tube is removably disposed within the second lumen and has a pull tube lumen which extends the entire length of the pull tube and which is capable of accommodating a guide wire, comprising the steps of:

(a) passing a distal end of the guide wire into an artery;

(b) disposing the pull tube about a proximal end of the guide wire;

(c) removing the pull tube from within the second lumen;

(d) advancing the catheter into the artery;

(e) removing the guide wire from the artery;

(f) advancing the catheter to a position appropriate for pumping.

15. A method for inserting a single lumen intra-aortic balloon catheter into an infant having a guide wire inserted into his or her femoral artery said intra-aortic balloon catheter comprising a catheter having distal and proximal ends, a balloon membrane having distal and proximal ends, a tip, and a pull tube, the proximal end of the balloon membrane is connected to the distal end of the catheter, the tip has a first proximal end, a second proximal end, a distal end, and a second lumen for accommodating a guide wire which extends from said distal end of the tip to said second proximal end, the distal end of the balloon membrane is connected to the first proximal end of the tip, the pull tube is removably disposed within the second lumen and has a pull tube lumen which extends the entire length of the pull tube and which is capable of accommodating a guide wire, comprising the steps of:

(a) disposing the pull tube about a proximal end of the guide wire;

(b) removing the pull tube from within the second lumen;

(c) advancing the catheter into the artery;

(d) removing the guide wire from the artery;

(e) advancing the catheter up the aortic passageway to a position appropriate for pumping.

16. A method for inserting a single lumen intra-aortic balloon catheter comprising a catheter having distal and proximal ends, a balloon membrane having distal and proximal ends, a tip, and a pull tube, the proximal end of the balloon membrane is connected to the distal end of the catheter, the tip has a first proximal end, a second proximal end, a distal end, and a self occluding lumen for accommodating a guide wire which extends from said distal of the tip end, to said second proximal end, the distal end of the balloon membrance is connected to the first proximal end of the tip, the pull tube is removably disposed within the second lumen and has a pull tube lumen which extends the entire length of the pull tube and which is capable of accommodating a guide wire, the self occluding lumen occludes along its entire length after the pull tube and the guide wire are removed, comprising the steps of:

(a) passing a distal end of the guide wire into an artery;

(b) disposing the pull tube about a proximal end of the guide wire;

(c) removing the pull tube from within the second lumen;

(e) advancing the catheter into the artery;

(e) removing the guide wire from the artery;

(f) advancing the catheter to a position appropriate for pumping.

17. The method as claimed in claims 13, 14, 15, or 16 further comprising the preliminary steps of inserting an angiographic needle into the artery, passing the guide through the needle into the artery, and then removing the needle.

18. The method as claimed in claims 13, 14, or 15 wherein the second lumen is self-occluding along its entire length.

* * * * *